(12) United States Patent
Zhang et al.

(10) Patent No.: US 11,730,840 B2
(45) Date of Patent: Aug. 22, 2023

(54) MOBILE DEVICES HAVING DISINFECTION LIGHT SOURCES

(71) Applicant: Bolb Inc., Livermore, CA (US)

(72) Inventors: Jianping Zhang, Arcadia, CA (US); Ling Zhou, Dublin, CA (US); Ying Gao, Fremont, CA (US)

(73) Assignee: BOLB INC., Livermore, CA (US)

( * ) Notice: Subject to any disclaimer, the term of this patent is extended or adjusted under 35 U.S.C. 154(b) by 188 days.

(21) Appl. No.: 17/169,552

(22) Filed: Feb. 8, 2021

(65) Prior Publication Data

US 2021/0162081 A1 Jun. 3, 2021

Related U.S. Application Data

(62) Division of application No. 16/377,141, filed on Apr. 5, 2019, now Pat. No. 11,071,797.

(51) Int. Cl.
*A61L 2/10* (2006.01)
*A61L 2/28* (2006.01)
*G01N 21/94* (2006.01)

(52) U.S. Cl.
CPC ............... *A61L 2/10* (2013.01); *A61L 2/28* (2013.01); *G01N 21/94* (2013.01); *A61L 2202/11* (2013.01); *A61L 2202/14* (2013.01); *A61L 2202/16* (2013.01)

(58) Field of Classification Search
CPC .......... A61L 2/10; A61L 2/28; A61L 2202/11; A61L 2202/14; A61L 2202/16; A61L 2/24; G01N 21/94; G01N 2021/945
See application file for complete search history.

(56) References Cited

U.S. PATENT DOCUMENTS

2021/0052757 A1* 2/2021 Baarman .................. A61L 2/10

* cited by examiner

*Primary Examiner* — Regina M Yoo
(74) *Attorney, Agent, or Firm* — J.C. Patents

(57) ABSTRACT

The present invention relates to mobile devices for disinfecting an object. The mobile device includes: one or more light sources for generating a disinfection light; a display; one or more processors coupled to the one or more light sources and display; and a non-transitory computer-readable medium comprising one or more sequences of instructions which, when executed by the one or more processors, causes steps to be performed including: determining a required dosage of the disinfection light; determining an exposure time of the disinfection light that corresponds to the required dosage of the disinfection light; illuminating the disinfection light on the surface; and displaying a disinfection map on the display to report a result of a disinfection process performed by the illumination of the disinfection light.

7 Claims, 10 Drawing Sheets

MOBILE DEVICES HAVING DISINFECTION LIGHT SOURCES

CROSS-REFERENCE TO PRIOR APPLICATIONS

This application is a divisional application of U.S. patent application Ser. No. 16/377,141, filed on Apr. 5, 2019, which is all hereby incorporated by reference in its entirety.

BACKGROUND

A. Technical Field

The present invention relates to disinfection devices, and more particularly, to mobile devices that have disinfection light sources.

B. Background of the Invention

UV light sources, such as UV light emitting diodes (LEDs), have been used in various applications, such as industrial and cosmetic curing, sterilization of harmful bacteria, indoor gardening, and treatment of human skin condition, so on. Ultraviolet germicidal irradiation (UVGI) is a disinfection technique that uses UV-C light, which has a wavelength range of 200-280 nm, to kill or inactivate microorganisms. More specifically, UVGI destroys nucleic acids and disrupts DNA of microorganisms, leaving them unable to perform vital cellular functions. UVGI can be used in various applications, such as water, food, and infected surfaces that may come in contact with human.

With the advent of mobile device technology and LED, the current mobile devices can have LEDs that generate UV-C light and batteries that supply sufficient electrical power to the LEDs so that the mobile devices may be used as a light source for UVGI. However, care must be taken when such mobile devices are used as the light sources of UVGI. For instance, exposure to UV-C light does not offer a natural avoidance response of human eyes, such as squinting eyes to bright light, and, can pose a threat to human eyes. In another example, excess exposure of human skin to UV-C light may result in painful burns on the skin.

In addition to the potential threats to human body, the mobile devices need to have a power control mechanism to optimize the usage of battery power. In general, the degree of inactivation by UVGI is directly related to the UV dosage incident on the surface of the object to be disinfected, where the dosage is a product of UV light irradiance and exposure time. Typically, dosages for a 90% kill of most bacteria and viruses range from 2,000 to 8,000 $\mu W \cdot s/cm^2$. As such, the mobile devices need to have a mechanism that ensures delivery of the required UV dosage and shuts offs the LED upon completion of the disinfection process so as to minimize the battery power consumption.

As such, there is a need for mobile devices that can provide UVGI for germicidal applications without inflicting damages to human and have a mechanism for minimizing the battery power consumption.

SUMMARY OF THE DISCLOSURE

In one aspect of the present invention, a mobile device for disinfecting an object includes: one or more light sources for generating a disinfection light; a display; one or more processors coupled to the one or more light sources and display; and a non-transitory computer-readable medium comprising one or more sequences of instructions which, when executed by the one or more processors, causes steps to be performed including: determining a required dosage of the disinfection light; determining an exposure time of the disinfection light that corresponds to the required dosage of the disinfection light; illuminating the disinfection light on the surface; and displaying a disinfection map on the display to report a result of a disinfection process performed by the illumination of the disinfection light.

In another aspect of the present invention, a method for disinfecting an object includes: determining a required dosage of a disinfection light that is generated by one or more light sources of a mobile device for disinfecting an object; determining an exposure time of the disinfection light that corresponds to the required dosage of the disinfection light; illuminating the disinfection light on a surface of the object; and displaying a disinfection map on a display of the mobile device to report a result of a disinfection process performed by the illumination of the disinfection light.

In another aspect of the present invention, a non-transitory computer-readable medium or media including one or more sequences of instructions which, when executed by one or more processors, causes steps to be performed including: determining a required dosage of a disinfection light that is generated by one or more light sources of a mobile device for disinfecting an object; determining an exposure time of the disinfection light that corresponds to the required dosage of the disinfection light; illuminating the disinfection light on a surface of the object; and displaying a disinfection map on a display of the mobile device to report a result of a disinfection process performed by the illumination of the disinfection light.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

DETAILED DESCRIPTION OF THE PREFERRED EMBODIMENTS

In the following description, for the purposes of explanation, specific details are set forth in order to provide an understanding of the invention. It will be apparent, however, to one skilled in the art that the invention can be practiced without these details. One skilled in the art will recognize that embodiments of the present invention, described below, may be performed in a variety of ways and using a variety of means. Those skilled in the art will also recognize additional modifications, applications, and embodiments are within the scope thereof, as are additional fields in which the invention may provide utility. Accordingly, the embodiments described below are illustrative of specific embodiments of the invention and are meant to avoid obscuring the invention.

A reference in the specification to "one embodiment" or "an embodiment" means that a particular feature, structure, characteristic, or function described in connection with the embodiment is included in at least one embodiment of the invention. The appearance of the phrase "in one embodiment," "in an embodiment," or the like in various places in the specification are not necessarily all referring to the same embodiment.

Figure 1A:
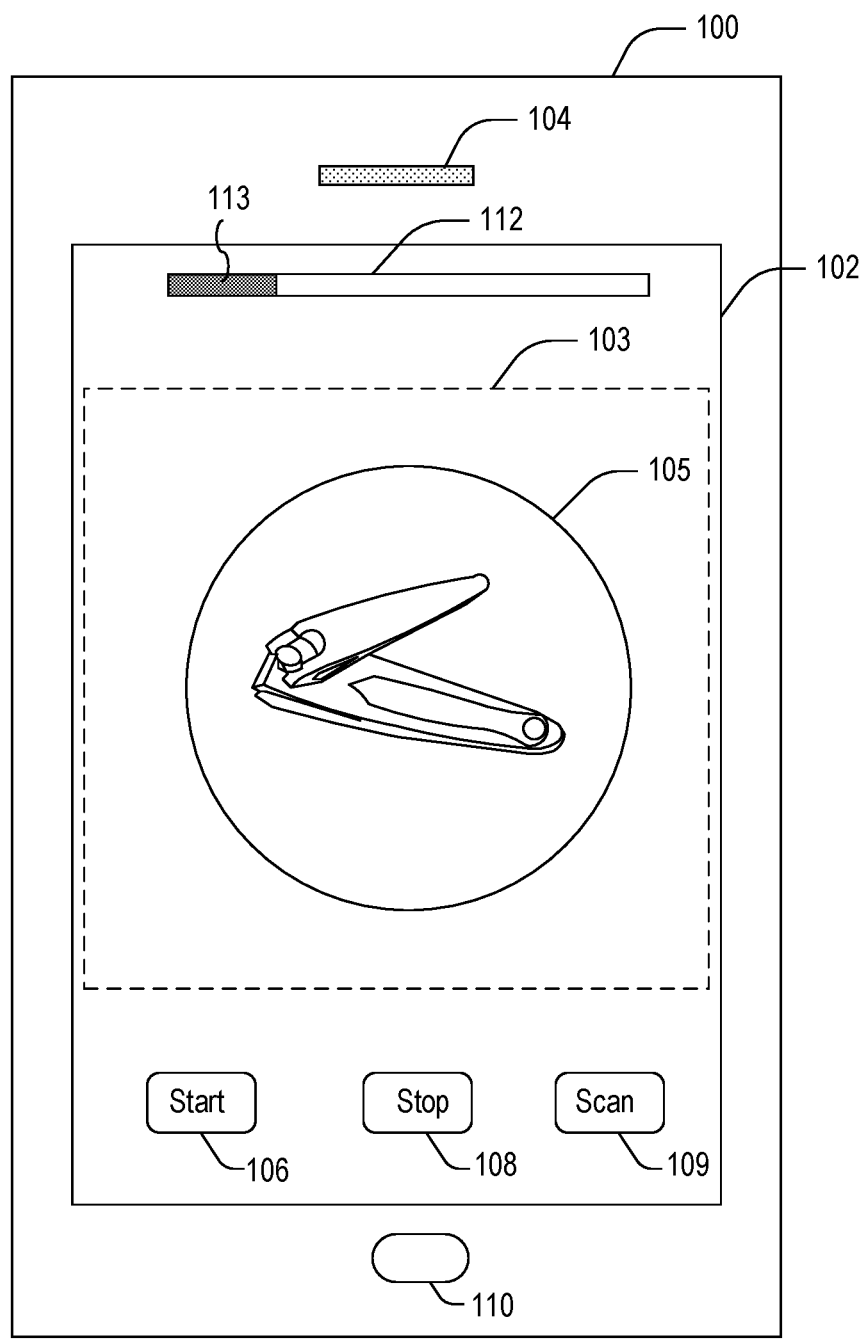
FIG. 1A shows a front view of a mobile device for germicidal applications according to embodiments of the present disclosure.
Figure 2:
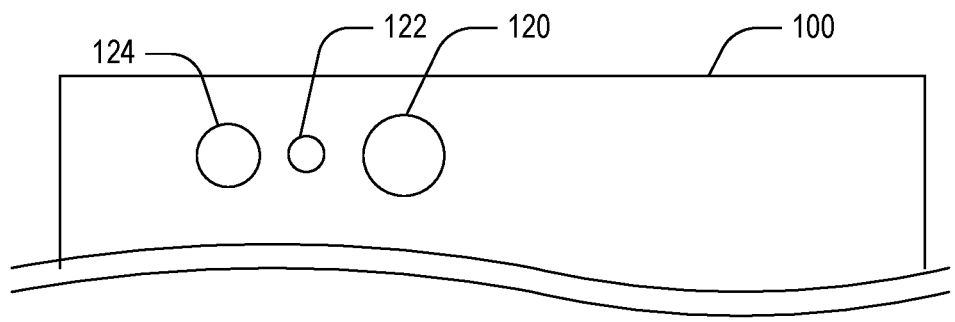
FIG. 2 shows a rear view of a mobile device for germicidal applications according to embodiments of the present disclosure.
Figure 3:
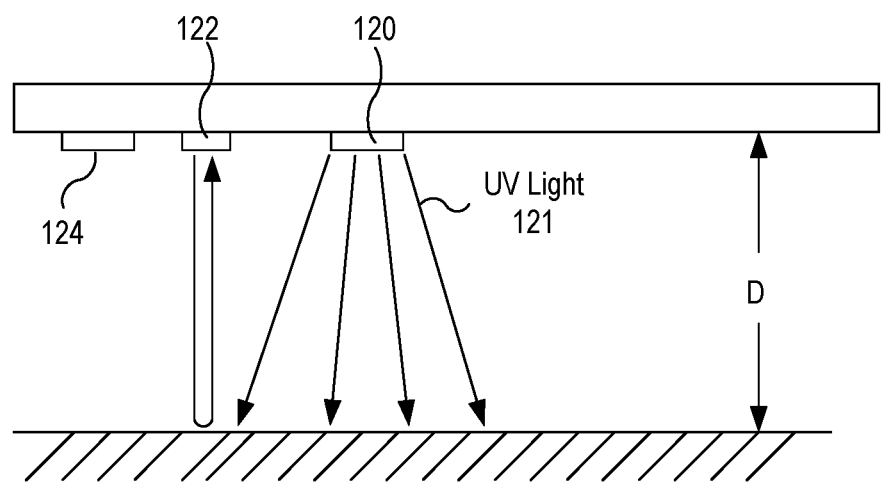
FIG. 3 shows a top view of a mobile device for germicidal applications according to embodiments of the present disclosure.

FIG. 1A shows a front view of a mobile device 100 for germicidal applications according to embodiments of the present disclosure. FIG. 2 shows a rear view of a mobile device 100 for germicidal applications according to embodiments of the present disclosure. For the purpose of illustration, the mobile device 100 is described as a mobile phone. However, it should be apparent to those of ordinary skill in the art that other suitable types of mobile devices may be used in place of the mobile phone. Hereinafter, the term germs collectively refers to bacteria, viruses, and other microorganisms that can cause infection and disease.

As depicted, the mobile device 100 may include: a display screen (or shorty display) 102 for displaying a graphic user interface (GUI); a push button 110 for controlling the mobile device 100; and a speaker 104 for outputting audio signals; a camera 124 for capturing an image; a light source 120 for generating disinfection light 121; and a distance meter 122 for measuring a distance D from the light source 120 to the surface of an object to be disinfected. For the purpose of illustration, the light source 120 is described as an LED and the disinfection light is described as a UV-C light, even though other suitable types of light sources and other wavelength range may be used to kill the germs. In embodiments, the light source 120 may include one LED for generating the disinfection light and/or another LED for generating a fluorescent light, as discussed below. In embodiments, the light source 120 may also include a LED that generates a visible light that is operated by another application installed in the mobile phone 100.

In embodiments, the GUI may be generated by an application that is installed in and running on the mobile device 100. In embodiments, the GUI may include: a start button 106; a stop button 108; a scan button 109; an image display area 103 for displaying an image captured by the camera 124; a status indicator 112 for indicating the status of disinfection process; and a disinfection area indicator 105 for indicating the area to be disinfected. As indicated, the disinfection area indicator 105 may be displayed on top of the image (such as nail clipper) captured by the camera 124, to thereby indicate the area to be disinfected.

In embodiments, a Vertical Cavity Surface Emitting LASER (VCSEL) and a time-of-flight sensor may be used as the distance meter 122, even though other suitable types of distance meters may be used to measure the distance D. In embodiments, the divergence angle of the light 121 from the light source 120 may be known in advance. As such, using the measured distance D, the disinfection area indicator 105 may be determined and displayed on the screen 102. In embodiments, the disinfection area indicator 105 may have various shapes, even though a circle is shown in FIG. 1A for the purpose of illustration.

In embodiments, the total radiant flux (or shortly, radiant flux) of the light 121 may be known in advance. Thus, based on the size of the disinfection area indicator 105, the irradiance of the disinfection light on the surface (which is the radiance flux divided by the surface area bounded by the disinfection area indicator 105) may be calculated. In embodiments, for a given dosage for killing germs, the required exposure time may be determined, as dosage is a product of UV irradiance and exposure time.

In embodiments, the light source 120 may also send fluorescent light, such as UV-A light, that may be used to scan (inspect) the surface for contamination. In embodiments, the user may touch the scan button 109 to illuminate the fluorescent light on the surface of the object and check if the surface is contaminated with foreign substances and/or germs. In embodiments, when the fluorescent light falls on the surface of the object, the foreign substance and/or germs may reflect or emit visible light, depending on the property of foreign substance and/or germs, which may be used to reveal the contamination of the surface.

Upon detecting the contamination, the user may use the mobile phone 100 to disinfect the object. In embodiments, when the user points the camera 124 toward the object to be disinfected, the mobile device 100 may capture the image of the object and identify the object. For instance, the mobile device 100 may have an artificial intelligence (AI) program that can recognize the shape of the object as a portion of human body, such as human eye, or recognize the texture of the object surface as human skin. In embodiments, the mobile device 100 determines the potential damages on the object, and, if the mobile device determines that the object should not be disinfected by the light 121, the mobile device 100 may give a warning signal through the speaker 104 and disable the start button 106. In embodiments, this warning system may prevent any potential damages to the human body or any other object.

Figure 1B:
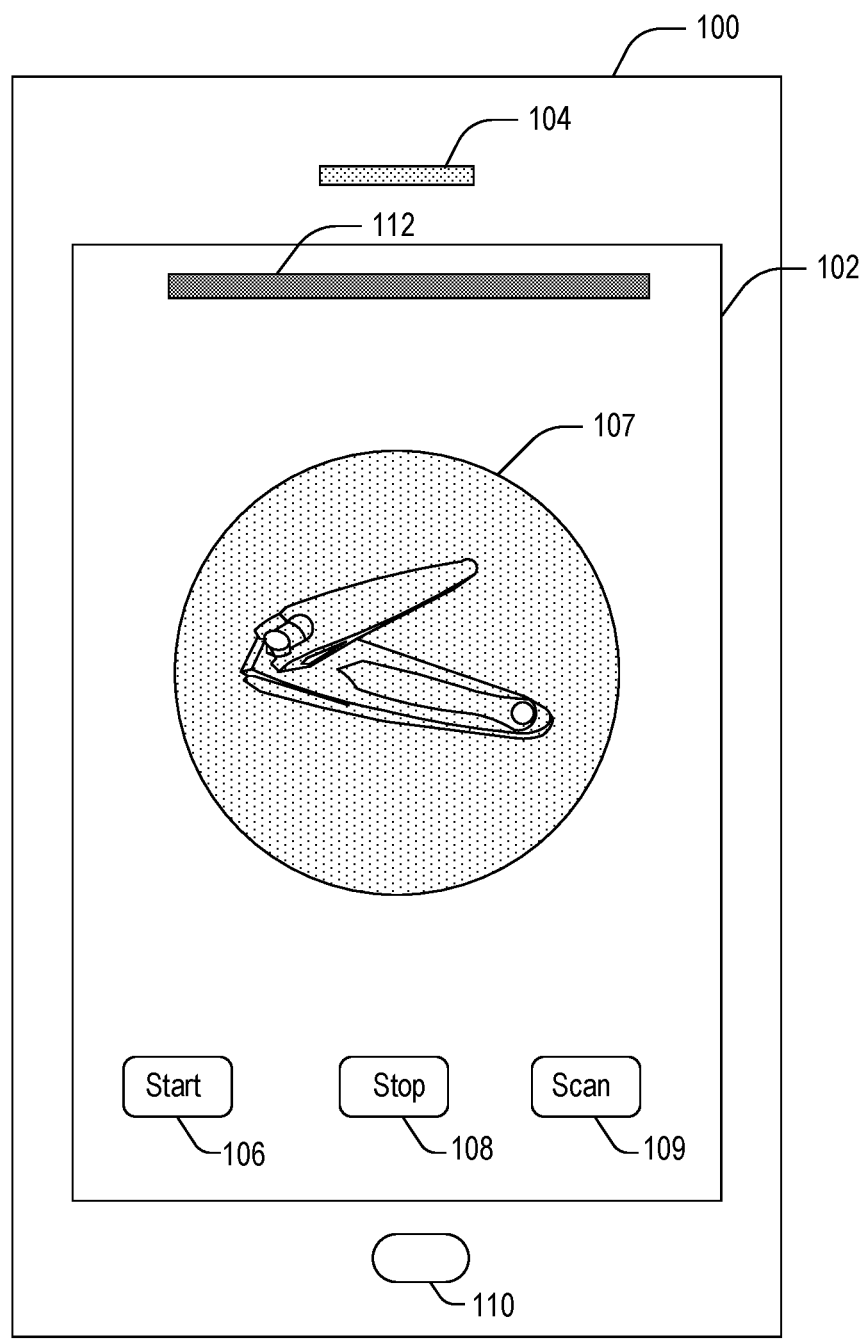
FIG. 1B shows a front view of a mobile device for germicidal applications according to embodiments of the present disclosure.

In embodiments, when the user locates the object within the disinfection area indicator 105, the mobile device 100 may calculate the required exposure time, based on the measure distance D. Then, in response to the user's click on the start button 106, the mobile device 100 may start the disinfection process by illuminating the disinfection light 121 toward the object. In embodiments, the length of the shaded bar 113 in the status indicator 112 may increase as the exposer time increases, indicating the disinfection progress. FIG. 1B shows a front view of a mobile device 100 according to embodiments of the present disclosure. As depicted, the status indicator 112 may indicate that the disinfection process is completed, i.e., the required exposure time has lapsed.

In embodiments, the disinfection process may be terminated either by the user or the mobile phone itself. In embodiments, the user may touch the stop button 108 to terminate the disinfection process. In embodiments, the mobile phone 100 may terminate the disinfection process when the required exposure time for the required dosage of the disinfection light has lapsed. In either case, in embodiments, the mobile device 100 may report the result of the disinfection process by displaying a disinfection map 107, as shown in FIG. 1B.

In embodiments, the disinfection map 107 may show an image of the object and an image of a disinfection area swept by the disinfection light during the disinfection process. In embodiments, the disinfection area may be filled with different colors to indicate the level of exposure (i.e., the amount of dosage of the disinfection light). In the case where the mobile phone 100 was stationary during the disinfection process, the disinfection map 107 may cover the same area as the disinfection area indicator 105, as shown in FIG. 1B. In embodiments, when the user may click the stop button 108 to abort the disinfection process before the disinfection process is completed, the image of the disinfection area in the disinfection map 107 may be filled with a first color (e.g. yellow), to indicate that the disinfection process is incomplete or terminated prematurely. In embodiments, the color filling the area may change progressively to indicate the disinfection progress.

In embodiments, the user may click the start button 106 again to resume the disinfection process. In such a case, the mobile device 100 may accumulate the amount of disinfection light incident on the disinfection area during the previous and current disinfection processes, and the status indicator 112 may show the accumulated dosage of the disinfection light. In embodiments, this feature allows the user to complete the disinfection process without restarting the process again, which may reduce the battery power consumption.

In embodiments, the user may set a desired dosage of the disinfection light. For instance, the user may enter the information of desired dosage, such as 40 mJ/cm$^2$, in a text field (not shown in FIG. 1A) in the GUI. Then, the mobile device 100 may calculate the corresponding exposure time, based on the calculated irradiance of the disinfection light, and deliver the desired dosage by illuminating the disinfection light during the exposure time.

In embodiments, the mobile device 100 may retrieve information of the threshold dosage from a data storage, calculate the threshold exposure time, based on the calculated irradiance of the disinfection light, and illuminate the disinfection light during the threshold exposure time.

Figure 4A:
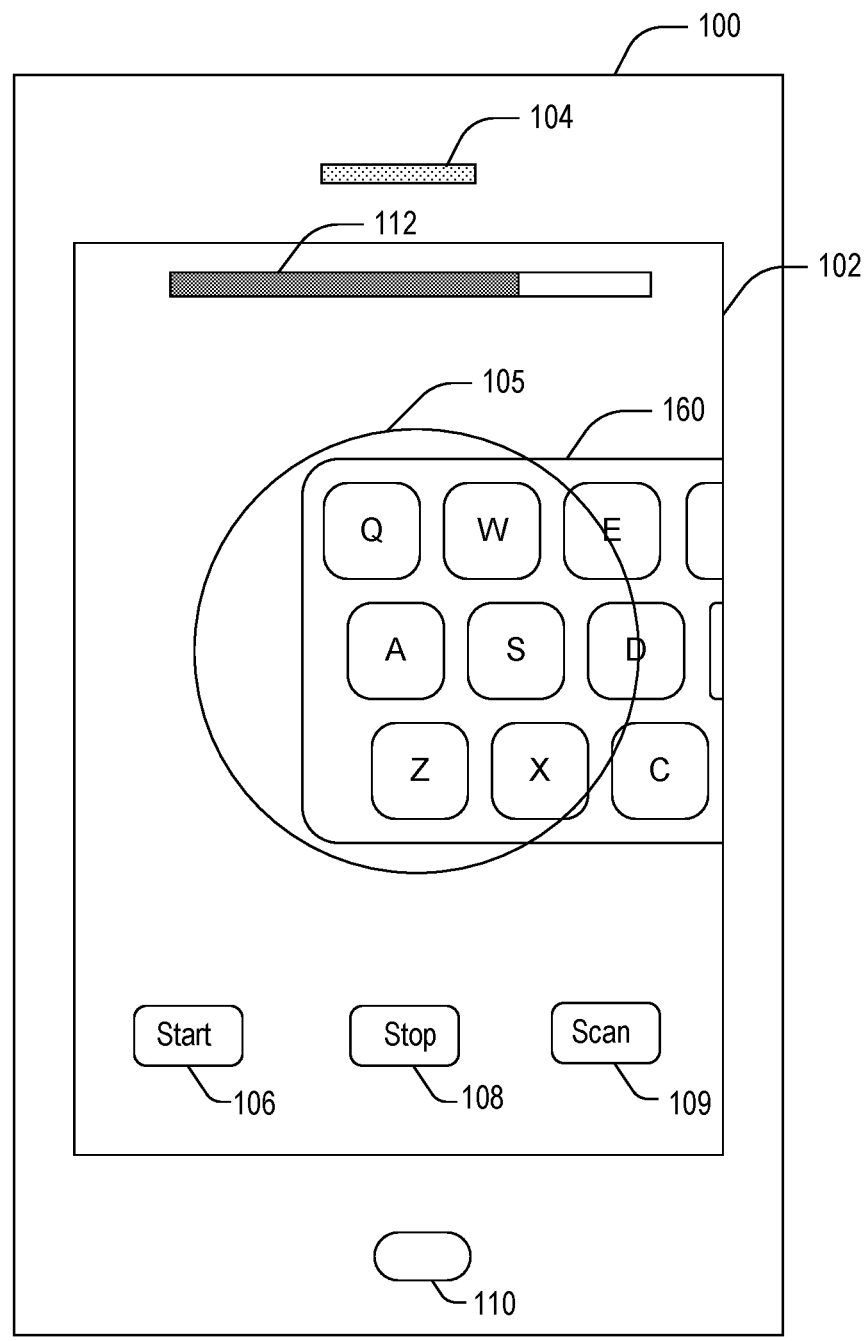
FIGS. 4A-4C show how to use a mobile device to disinfect an elongated object according to embodiments of the present disclosure.
Figure 4B:
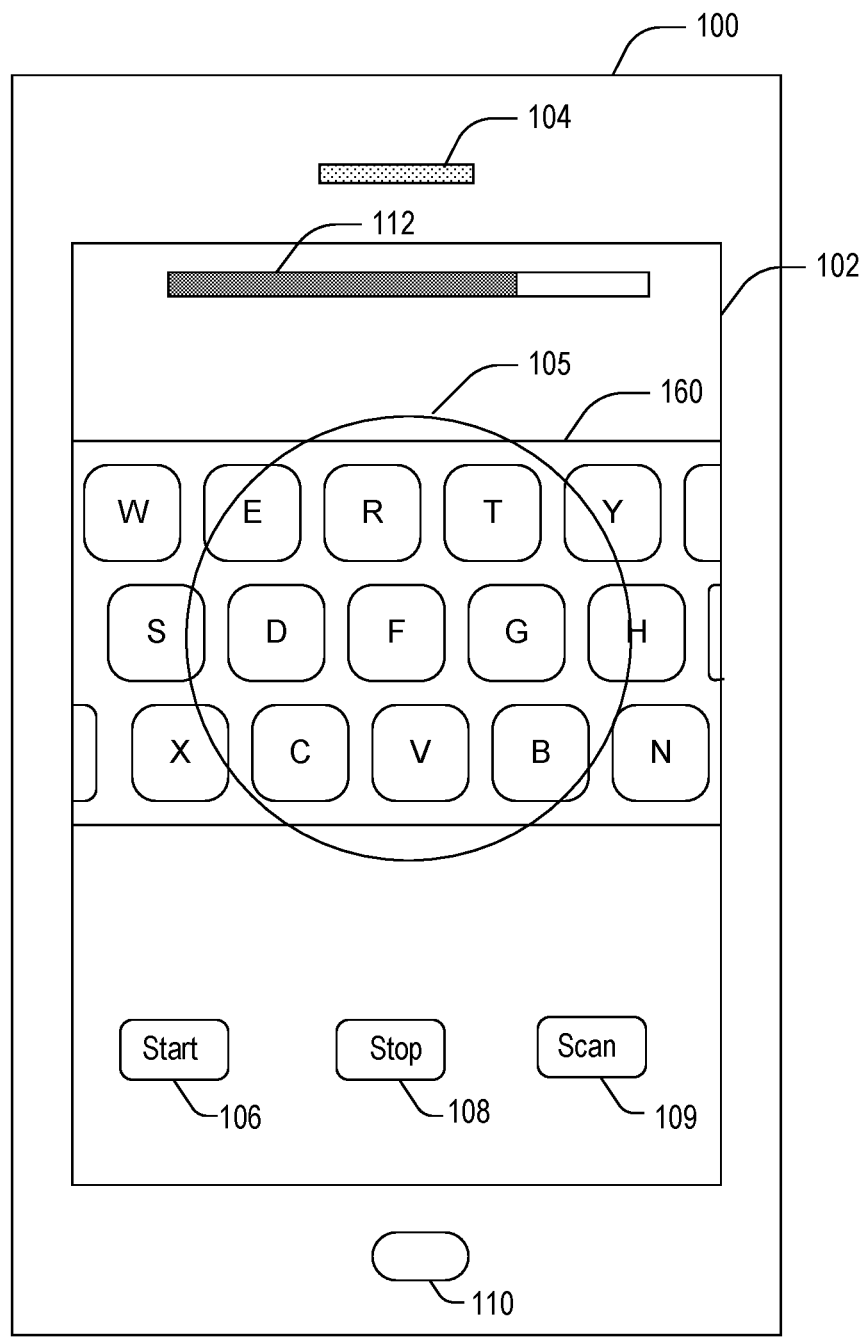
Figure 4C:
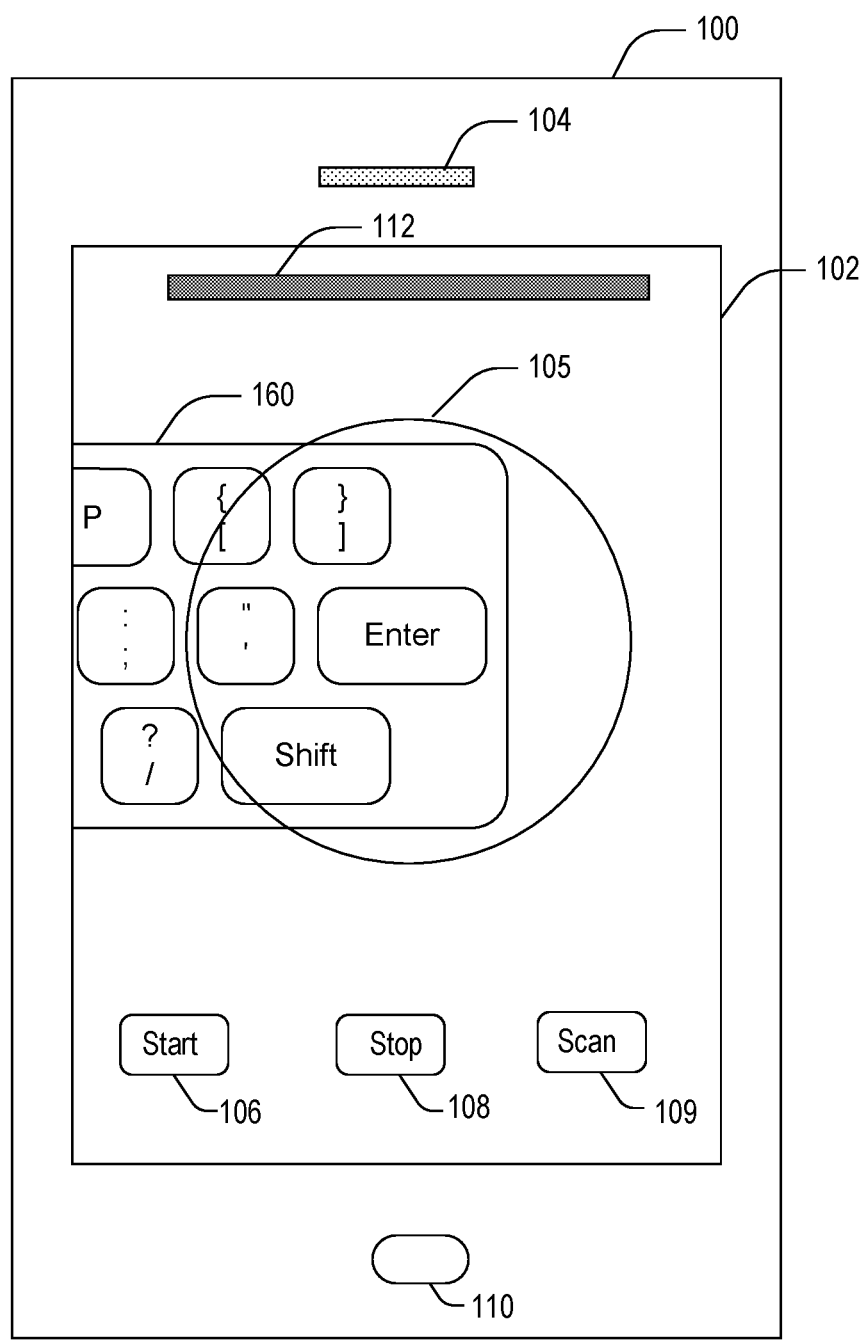

FIGS. 4A-4C show how to use a mobile device to disinfect an elongated object according to embodiments of the present disclosure. In embodiments, for the purpose of illustration, the mobile device 100 is used to disinfect a computer keyboard. However, it should be apparent to those of ordinary skill in the art that other types of elongated objects may be disinfected by the same manner as the keyboard is disinfected.

In embodiments, the user may scan the surface of the keyboard 160 to determine the contamination, using the fluorescent light from the light source 120. Also, using the AI program, the mobile phone 100 may determine whether the object should not be disinfected by the disinfection light 121. Upon finding the contamination and determining that the object is not going to be damaged by the disinfection light, the user may locate the leftmost portion of the keyboard 160 inside the disinfection area indicator 105 and touch the start button 106 to start the disinfection process, as depicted in FIG. 4A.

In embodiments, the user may move the mobile phone 100 to disinfect different portion of the keyboard 160 before the status indicator 112 indicates that the disinfection process is completed. In embodiments, the mobile phone 100 may detect the motion and reset the status indicator 112 each time a motion is detected. For instance, as shown in FIG. 4B, when the user moves the mobile phone 100 toward the central portion of the keyboard 160, the mobile phone 100 may recognize that the user intends to disinfect a different portion of the keyboard, reset the status indicator 112, and start disinfecting the central portion.

In embodiments, the user may repeat the steps of moving and disinfecting different portions of the keyboard 160 until the entire portion of the keyboard 160 is disinfected. In embodiments, the mobile phone 100 may stop disinfecting the object when the user stops moving the mobile phone 100 and the required exposure time for disinfecting the last portion of the keyboard lapses. As depicted in FIG. 4C, the status indicator 112 may indicate that the disinfection process for the last portion of the keyboard 160 is complete. In alternative embodiments, the user may stop the disinfection process by touching the stop button 108 at any time during the disinfection process.

Figure 5:
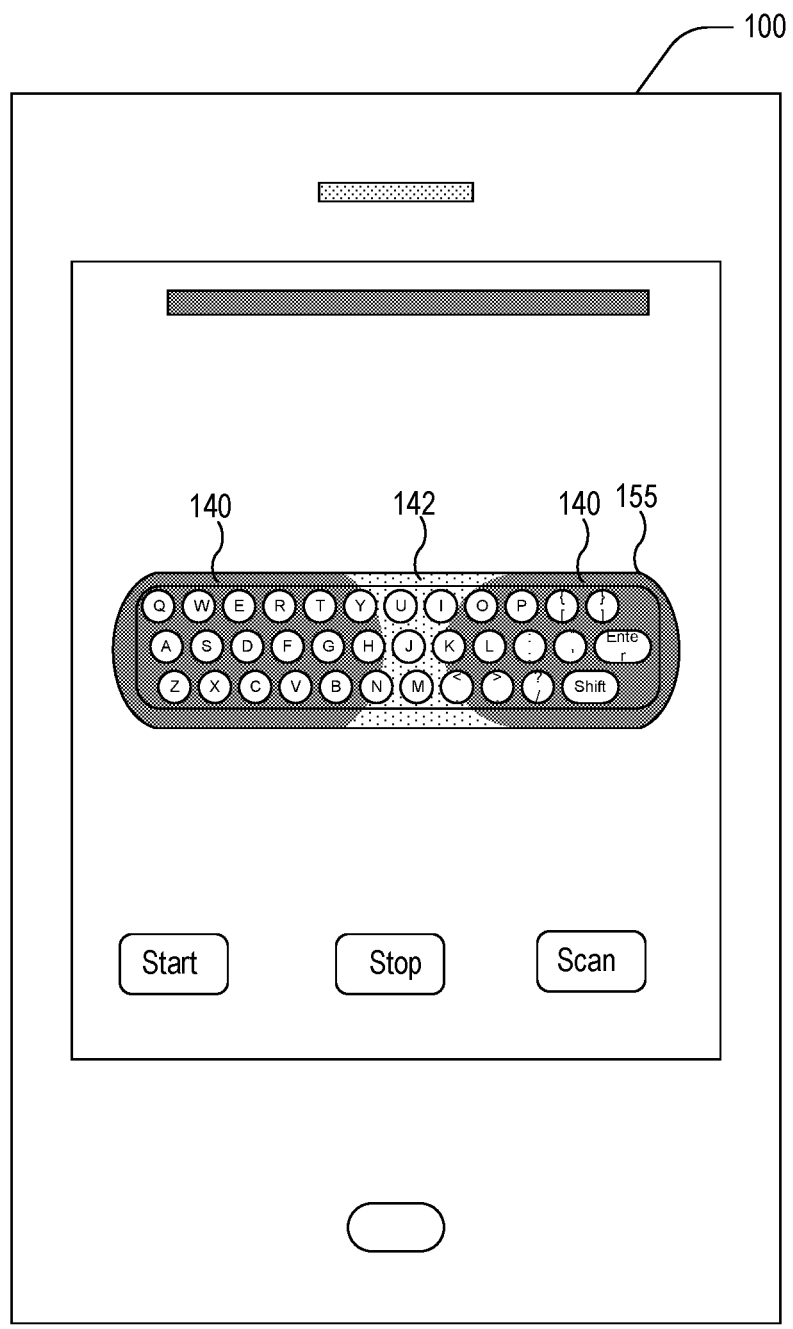
FIG. 5 shows a front view of a mobile device for germicidal applications according to embodiments of the present disclosure.

FIG. 5 shows a front view of a mobile device for germicidal applications according to embodiments of the present disclosure. As depicted, upon terminating the disinfection process of the keyboard 160, the mobile phone 100 may report the result of the disinfection process by displaying a disinfection map 155. In embodiments, the disinfection map 155 may include the panoramic image of the keyboard and an image of a disinfection area superimposed on the image of the keyboard, where the disinfection area represents the region swept by the disinfection light during the disinfection process. In embodiments, the disinfection area in the disinfection map 155 be filled with different colors to indicate the level of exposure (i.e., the amount of dosage of the disinfection light). In embodiments, during the disinfection process, it may be possible that the user moved the mobile phone 100 before a portion of the keyboard is not disinfected completed, i.e., the user moved the mobile phone prematurely so that a region 142 did not receive the threshold dosage of disinfection light before the mobile phone was moved to a different region. In embodiments, the image of the disinfection area in the disinfection map 155 may be filled with different colors to distinguish a region, such as 142, that did not receive the required dosage of light for killing the germs, from a region(s), such as 140, that received the required dosage.

In embodiments, the user may disinfect only the region 142 in a subsequent disinfection process. In embodiments, when the user locates the region 142 within the disinfection area indicator 155 and touches the start button 106, the mobile device 100 may start illuminating and measuring the amount of the disinfection light incident on the surface. In embodiments, the mobile device 100 may accumulate the amount of disinfection light incident on the disinfection area during the previous and current disinfection processes, and the status indicator 112 may show the accumulated dosage of the disinfection light. In embodiments, this feature allows the user to complete the disinfection process without restarting the process over the entire keyboard 160 again, which may reduce the battery power consumption.

Figure 6:
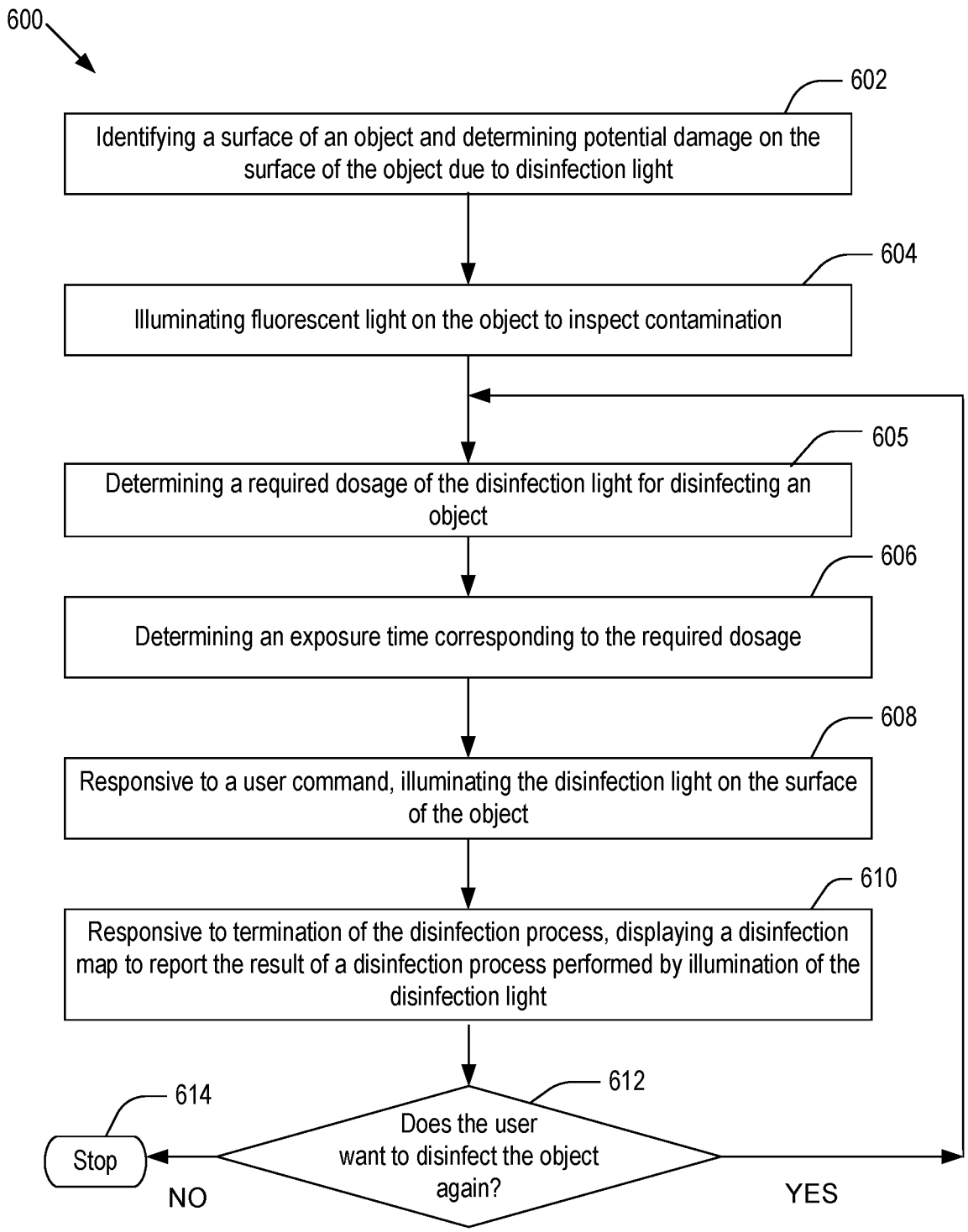
FIG. 6 shows a flowchart of an exemplary process for disinfecting an object according to embodiments of the present disclosure.

FIG. 6 shows a flowchart 600 of an exemplary process for disinfecting an object according to embodiments of the present disclosure. The process starts at step 602. At step 602, the mobile device 100 may identify the surface of an object and determine whether the surface can be disinfected by the disinfection light, such as UV-C, i.e., the potential damage on the surface by the disinfection light is accessed.

In embodiments, the AI program installed in the mobile phone 100 may recognize the shape of the object as a portion of a human body, such as human eye, or recognize the texture of the object surface as human skin. In embodiments, if the mobile phone 100 determines that the object cannot be disinfected, the user may be given a warning signal through the speaker 104 and the start button 106 may be disabled.

At step 604, the user may scan the surface of the object for contamination. In embodiments, the user may illuminate the fluorescent light, such as UV-A, from the light source 120 on the surface of the object to inspect contamination on the surface. In embodiments, the light source 120 may include one LED that generates both the disinfection light and the fluorescent light. In embodiments, the light source 120 may include one LED for generating the disinfection light and another LED for generating the fluorescent light. It should be apparent to those of ordinary skill in the art that the light source 120 may include any suitable number and type of LEDs. For instance, the light source 120 may also include a LED that generates the visible light. In embodiments, the step 604 may be skipped.

At step 605, the mobile device 100 may determine the required dosage of the disinfection light. In embodiments, the user may enter the information of desired dosage into the mobile device 100, preferably through the GUI on the display 102. In embodiments, the mobile device 100 may retrieve information of the threshold dosage for killing the germs from a data storage in the mobile device 100. Then, the mobile device 100 may use either the desired or threshold dosage as the required dosage for disinfecting the object.

At step 606, the mobile phone 100 may determine an exposure time corresponding to the required dosage. In embodiments, the distance meter 122 may measure the distance D between the light source 120 and the surface to be disinfected. Then, based on the given total radiant flux from the light source 120 and the size of the disinfection area indicator 105, the mobile phone 100 may calculate the light intensity (irradiance) of the disinfection light on the surface. Also, the exposure time for the required dosage may be calculated as the required dosage is a product of irradiance and exposure time.

At step 608, when the user touches the start button 106 (i.e., the user's command), the mobile device 100 may start illuminating the disinfection light on the surface of the object. Then, in embodiments, the user may terminate the disinfection process by touching the stop button 108 or the mobile phone 100 may automatically terminate the disinfection process when the exposure time lapses, i.e., the surface received the required dosage of the disinfection light.

At step 610, responsive to termination of the disinfection process, the mobile device 100 may display the disinfection map 107 or 155 to report the result of the disinfection process. In embodiments, the mobile phone 100 may be stationary during the disinfection process. In such a case, the disinfection map 107 may cover the same area as the disinfection area indicator 105. In embodiments, the mobile phone 100 may be in motion during the disinfection process to disinfect an elongated object. In such a case, the disinfection map 155 may include a panoramic image of the object and an image of a disinfection area, where the disinfection area represents the region swept by the disinfection light and is superimposed on the panoramic image of the object. In embodiments, the image of the disinfection area in the disinfection map 107 or 155 may be filled with different colors to indicate the level of disinfection (or equivalently the dosage of light incident on the surface).

At step 612, the user may decide whether to disinfect the object again. For instance, the user may want to disinfect the area 140 that did not receive the threshold dosage of the disinfection light. If the answer to the step 612 is negative, the mobile phone 100 may stop the disinfection process. Otherwise, the process may proceed to step 606.

Figure 7:
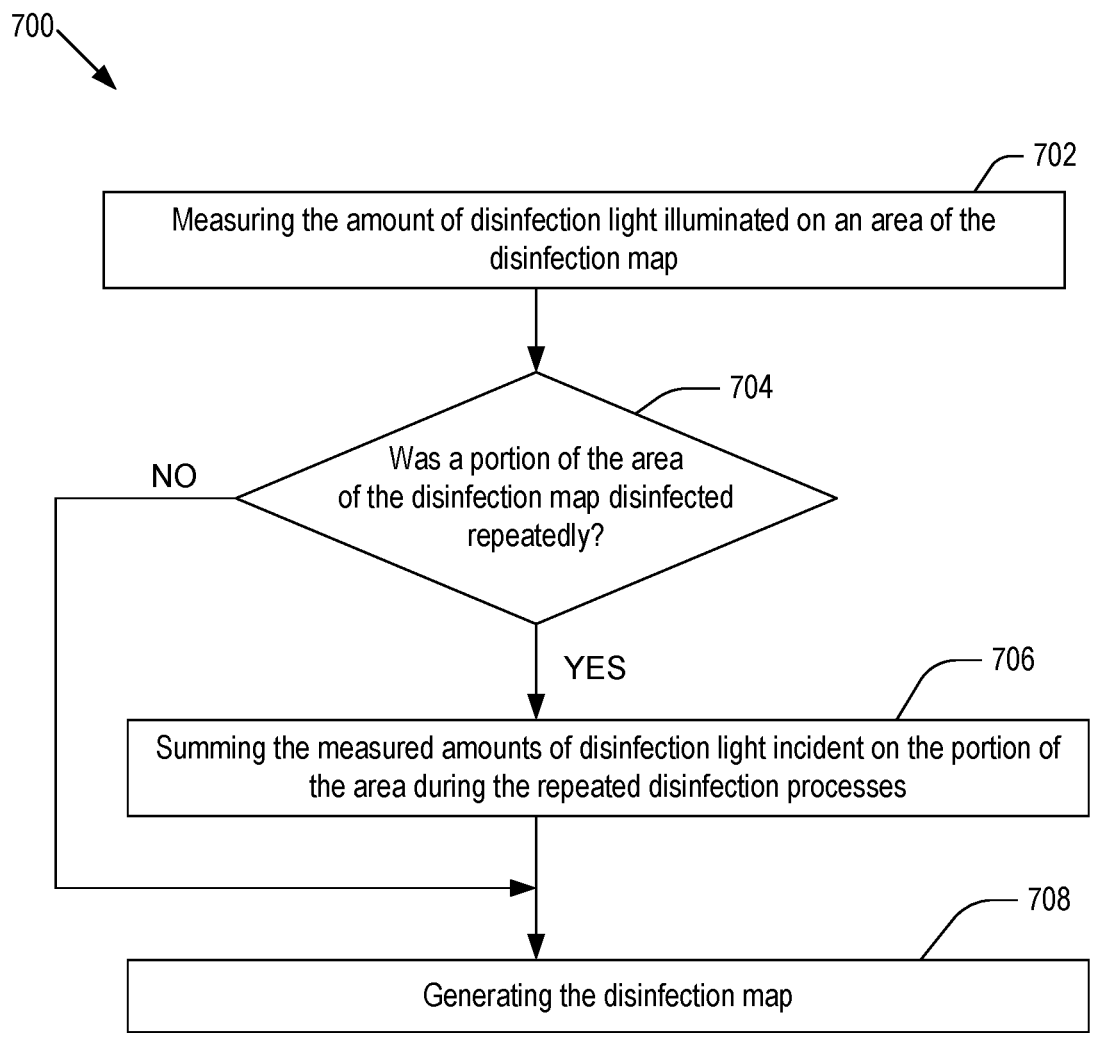
FIG. 7 shows a flowchart of an exemplary process for performing a step in FIG. 6 according to embodiments of the present disclosure.

In embodiments, as discussed in conjunction with step 612, the user may resume the disinfection process. For instance, the user may disinfect again the uncompleted region 142 that did not receive the threshold dosage of the disinfection light instead of disinfecting the entire keyboard 160. In such a case, the user may repeat disinfecting the region 142 only and the mobile device 100 may accumulate the amount of disinfection light received by the area 142 during the previous and current disinfection processes. FIG. 7 shows a flowchart 700 of an exemplary process for performing the step 610 in FIG. 6 according to embodiments of the present disclosure. As depicted, at step 702, the mobile device 100 may measure the amount of the disinfection light illuminated on an area, such as uncompleted region 142, of the disinfection map 155. At step 704, it may be determined whether a portion of the area in the disinfection map 155, such as the region 142, is disinfected repeatedly. By way of example, the user may disinfect only the region 140 in a subsequent disinfection process. If the answer to the step 704 is positive, the mobile device 100 may sum the amounts of disinfection light incident on the portion of the area during the repeated disinfection processes, i.e., the amounts of light incident on the portion of the area may be accumulated. Then, at step 708, the disinfection map may be generated. If the answer to step 704 is negative, the process proceeds to step 708. In embodiments, the accumulation process at step 708 may allow the user to selectively disinfect the uncompleted region 142, instead of disinfecting the whole area in the disinfection map 155.

In embodiments, as discussed above, the steps 702-708 may be performed when the user repeats disinfecting the nail clipper since the disinfection process was terminated prematurely in the previous disinfection process.

In one or more embodiments, aspects of the present patent document may be directed to, may include, or may be implemented on one or more mobile devices (or computing systems). A mobile device system/computing system may include any instrumentality or aggregate of instrumentalities operable to compute, calculate, determine, classify, process, transmit, receive, retrieve, originate, route, switch, store, display, communicate, manifest, detect, record, reproduce, handle, or utilize any form of information, intelligence, or data. For example, a computing system may be or may include a personal computer (e.g., laptop), tablet computer, mobile phone, personal digital assistant (PDA), smart watch, camera, or any other suitable device and may vary in size, shape, performance, functionality, and price. The computing system may include random access memory (RAM), one or more processing resources such as a central processing unit (CPU) or hardware or software control logic, ROM, and/or other types of memory. Additional components of the computing system may include one or more disk drives, one or more network ports for communicating with external devices as well as various input and output (I/O) devices, such as a keyboard, a mouse, touchscreen and/or a video display. The computing system may also include one or more buses operable to transmit communications between the various hardware components.

Figure 8:
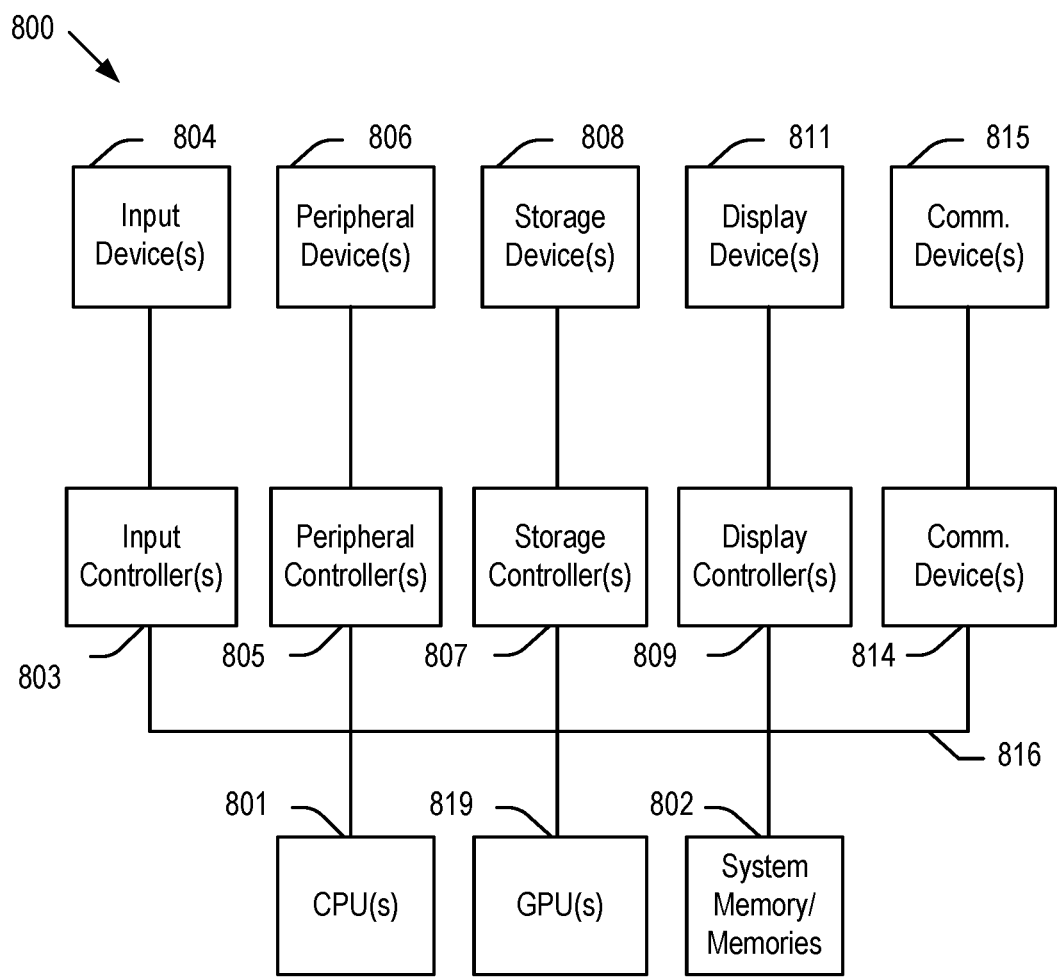
FIG. 8 shows a simplified block diagram of a UV light system according to embodiments of the present disclosure.

FIG. 8 depicts a simplified block diagram of a mobile device (or computing system) according to embodiments of the present disclosure. It will be understood that the functionalities shown for system 800 may operate to support various embodiments of a computing system—although it shall be understood that a computing system may be differently configured and include different components, including having fewer or more components as depicted in FIG. 8.

As illustrated in FIG. 8, the computing system 800 includes one or more central processing units (CPU) 801 that provides computing resources and controls the computer. CPU 801 may be implemented with a microprocessor or the like, and may also include one or more graphics processing units (GPU) 819 and/or a floating-point coprocessor for mathematical computations. System 800 may also include a system memory 802, which may be in the form of random-access memory (RAM), read-only memory (ROM), or both.

A number of controllers and peripheral devices may also be provided, as shown in FIG. 8. An input controller 803 represents an interface to various input device(s) 804, such as a keyboard, mouse, touchscreen, and/or stylus. The computing system 800 may also include a storage controller 807 for interfacing with one or more storage devices 808 each of which includes a storage medium such as magnetic tape or disk, or an optical medium that might be used to record programs of instructions for operating systems, utilities, and applications, which may include embodiments of programs that implement various aspects of the present disclosure. Storage device(s) 808 may also be used to store processed data or data to be processed in accordance with the disclosure. The system 800 may also include a display controller 809 for providing an interface to a display device 811, which may be a cathode ray tube (CRT), a thin film transistor (TFT) display, organic light-emitting diode, electroluminescent panel, plasma panel, or other type of display. The computing system 800 may also include one or more peripheral controllers or interfaces 805 for one or more peripherals 806. Examples of peripherals may include one or more printers, scanners, input devices, output devices, sensors, and the like. A communications controller 814 may interface with one or more communication devices 815, which enables the system 800 to connect to remote devices through any of a variety of networks including the Internet, a cloud resource (e.g., an Ethernet cloud, a Fiber Channel over Ethernet (FCoE)/Data Center Bridging (DCB) cloud, etc.), a local area network (LAN), a wide area network (WAN), a storage area network (SAN) or through any suitable electromagnetic carrier signals including infrared signals.

In the illustrated system, all major system components may connect to a bus 816, which may represent more than one physical bus. However, various system components may or may not be in physical proximity to one another. For example, input data and/or output data may be remotely transmitted from one physical location to another. In addition, programs that implement various aspects of the disclosure may be accessed from a remote location (e.g., a server) over a network. Such data and/or programs may be conveyed through any of a variety of machine-readable medium including, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices.

While the invention is susceptible to various modifications and alternative forms, specific examples thereof have been shown in the drawings and are herein described in detail. It should be understood, however, that the invention is not to be limited to the particular forms disclosed, but to the contrary, the invention is to cover all modifications, equivalents, and alternatives falling within the scope of the appended claims.

What is claimed is:

1. A method for disinfecting an object, comprising:
   determining a required dosage of a disinfection light that is generated by one or more light sources of a mobile device for disinfecting an object;
   determining an exposure time of the disinfection light that corresponds to the required dosage of the disinfection light;
   illuminating the disinfection light on a surface of the object; and
   displaying a disinfection map on a display of the mobile device to report a result of a disinfection process performed by the illumination of the disinfection light.

2. The method as recited in claim 1, further comprising:
   identifying the surface of the object to determine a potential damage on the surface of the object by the disinfection light.

3. The method as recited in claim 1, further comprising:
   illuminating a fluorescent light generated by the one or more lights sources on the surface of the object to inspect contamination on the surface of the object before determining the required dosage of the disinfection light.

4. The method as recited in claim 1, wherein the step of determining an exposure time includes:
   measuring a distance between the one or more light sources and the surface of the object;
   determining irradiance of the disinfection light on the surface of the object based on the measured distance; and
   calculating the exposure time based on the irradiance and required dosage of the disinfection light.

5. The method as recited in claim 1, wherein the step of displaying a disinfection map includes displaying an image of the object and an image of a disinfection area that is swept by the disinfection light during the disinfection process.

6. The method as recited in claim 5, wherein the step of displaying an image of a disinfection area includes filling the disinfection area with one or more colors to indicate dosage levels of the disinfection light incident on the disinfection area during the disinfection process.

7. The method as recited in claim 5, wherein the step of displaying an image of a disinfection area includes:
   responsive to repeated illuminations of the disinfection light on a portion of the disinfection area, summing amounts of the disinfection light incident on the portion of the disinfection area during the repeated illuminations.

* * * * *